US009855359B2

(12) United States Patent
Liu

(10) Patent No.: US 9,855,359 B2
(45) Date of Patent: Jan. 2, 2018

(54) ANALYTE SENSORS WITH ETHYLENE OXIDE IMMUNITY

(71) Applicant: Verily Life Sciences LLC, Mountain View, CA (US)

(72) Inventor: Zenghe Liu, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 275 days.

(21) Appl. No.: 14/138,379

(22) Filed: Dec. 23, 2013

(65) Prior Publication Data

US 2015/0177177 A1 Jun. 25, 2015

(51) Int. Cl.
| | |
|---|---|
| *G01N 27/327* | (2006.01) |
| *A61L 2/20* | (2006.01) |
| *A61B 5/1486* | (2006.01) |
| *C12Q 1/00* | (2006.01) |
| *A61B 5/145* | (2006.01) |
| *A61B 5/00* | (2006.01) |

(52) U.S. Cl.
CPC ............ *A61L 2/206* (2013.01); *A61B 5/1486* (2013.01); *A61B 5/14532* (2013.01); *A61B 5/14546* (2013.01); *C12Q 1/006* (2013.01); *A61B 5/682* (2013.01); *A61B 5/6821* (2013.01)

(58) Field of Classification Search
CPC ............ G01N 27/3274; G01N 27/327; G01N 27/3272; A61L 2/206; A61B 5/14532; A61B 5/14546; A61B 5/1486
See application file for complete search history.

(56) References Cited

U.S. PATENT DOCUMENTS

| | | | |
|---|---|---|---|
| 5,034,330 | A | 7/1991 | Yamori |
| 5,053,225 | A | 10/1991 | Miyasaka |
| 5,264,104 | A | 11/1993 | Gregg |
| 6,268,161 | B1 * | 7/2001 | Han ..................... A61B 5/0031 435/14 |
| 6,653,358 | B2 | 11/2003 | Bruza |
| 7,959,791 | B2 | 6/2011 | Kajer |
| 8,088,595 | B2 | 1/2012 | Ibey |
| 8,133,435 | B2 | 3/2012 | Reynolds |
| 8,241,819 | B2 | 8/2012 | Lowe |
| 8,385,998 | B2 | 2/2013 | Zhang |
| 8,437,829 | B2 | 5/2013 | Mao |
| 8,506,779 | B2 | 8/2013 | Kahn et al. |
| 8,562,801 | B2 | 10/2013 | Boeck |
| 8,579,816 | B2 | 11/2013 | Kamath |
| 2004/0256227 | A1 | 12/2004 | Shin |
| 2007/0059196 | A1 | 3/2007 | Brister |
| 2007/0111196 | A1 * | 5/2007 | Alarcon ............... A61L 2/0011 435/4 |
| 2007/0244379 | A1 | 10/2007 | Boock |
| 2008/0020454 | A1 | 1/2008 | Uematsu |
| 2008/0154101 | A1 | 6/2008 | Jain |
| 2008/0179187 | A1 | 7/2008 | Ouyang |
| 2008/0281178 | A1 | 11/2008 | Chuang |
| 2009/0232700 | A1 | 9/2009 | Alarcon |
| 2009/0257911 | A1 * | 10/2009 | Thomas ............. A61B 5/14532 422/22 |
| 2010/0051479 | A1 | 3/2010 | Heller |
| 2010/0160756 | A1 | 6/2010 | Petisce |
| 2010/0166607 | A1 | 7/2010 | Bartetzko |
| 2010/0175992 | A1 | 7/2010 | Shah |
| 2010/0267161 | A1 | 10/2010 | Wu |
| 2010/0279377 | A1 | 11/2010 | Shah |
| 2010/0280347 | A1 | 11/2010 | Shah |
| 2011/0082356 | A1 | 4/2011 | Yang |
| 2011/0136929 | A1 | 6/2011 | Chow |
| 2012/0088997 | A1 | 4/2012 | Guiseppi-Ellie |
| 2012/0157801 | A1 | 6/2012 | Hoss |
| 2012/0190950 | A1 | 7/2012 | Yang |
| 2012/0201755 | A1 | 8/2012 | Rozakis |
| 2012/0245444 | A1 | 9/2012 | Otis |
| 2012/0283537 | A1 | 11/2012 | Petisce et al. |
| 2012/0283538 | A1 | 11/2012 | Rose |
| 2012/0328473 | A1 | 12/2012 | Thomas et al. |
| 2013/0011460 | A1 | 1/2013 | Liu |
| 2013/0040404 | A1 | 2/2013 | Crane |

FOREIGN PATENT DOCUMENTS

| | | |
|---|---|---|
| WO | 2009042631 A2 | 4/2009 |
| WO | 2009126942 | 10/2009 |
| WO | 2010005290 | 1/2010 |
| WO | WO2012115501 A1 | 8/2012 |
| WO | WO2013012687 A3 | 1/2013 |
| WO | 2013-180633 A1 | 12/2013 |

OTHER PUBLICATIONS

International Search Report for PCT/US2014/071170, dated Mar. 13, 2015.
Yu et al., "Use of Hydrogel Coating to Improve the Performance of Implanted Glucose Sensors" Biosensors and Bioelectronics, 2008, 1278-1284 (Jan. 7, 2008).
Slaughter, "Fabrication of Nanoindented Electrodes for Glucose Detection" Journal of Diabetes Science and Technology, 2010, 4, 2, 320-327 (Mar. 2010).
Akkaya, B. et al. "Functional polymeric supports for immobilization of cholesterol oxidase" Biochemical EngineeringJournal43 (2009) 333-337.
Jusoh, Norhana et al., "Improvement of Glucose Biosensor Performances Using Poly(hydroxyethylmethacrylate) Outer Membrane," International Journal of Biology and Biomedical Engineering, Issue 1, vol. 6, pp. 77-86 (2012).
Gil, M.H., et al., "Immobilization of Glucose Oxidase on Thin-Film Gold Electrodes Produced by Magnetron Sputtering and Their Application in an Electrochemical Biosensor," Biotechnology Techniques, vol. 13, pp. 595-599 (1999).
Hall, C.E. et al., "Covalent Immobilisation of Glucose Oxidase on Methacrylate Copolymers for Use in an Amperometric Glucose Sensor," Analytica Chimica Acta, vol. 281, pp. 645-653 (1993).
Tseng, et al., "Fabrication of implantable, enzyme-immobilized glutamate sensors for the monitoring of glutamate concentration changes in vitro and in vivo" Molecules, (Jun. 5, 2014) pp. 7341-7355, whole document.

(Continued)

*Primary Examiner* — Gurpreet Kaur
(74) *Attorney, Agent, or Firm* — McDonnell Boehnen Hulbert & Berghoff LLP

(57) ABSTRACT

Analyte sensors capable of undergoing sterilization with ethylene oxide are provided. The analyte sensors can include one or more polymer membranes having a nucleophilic group.

15 Claims, 1 Drawing Sheet

(56) References Cited

OTHER PUBLICATIONS

Yan, et al., "Transparent and flexible glucose biosensor via layer-by-layer assembly of multi-wall carbon nanotubes and glucose oxidase" Electrochemistry Communications, (2007) pp. 1269-1275, vol. 9, No. 6.

Yao, H. et al. "A Soft Hydrogel Contact Lens With an Encapsulated Sensor for Tear Glucose Monitoring" MEMS, 2012, 769-772 (Jan. 29, 2012).

\* cited by examiner

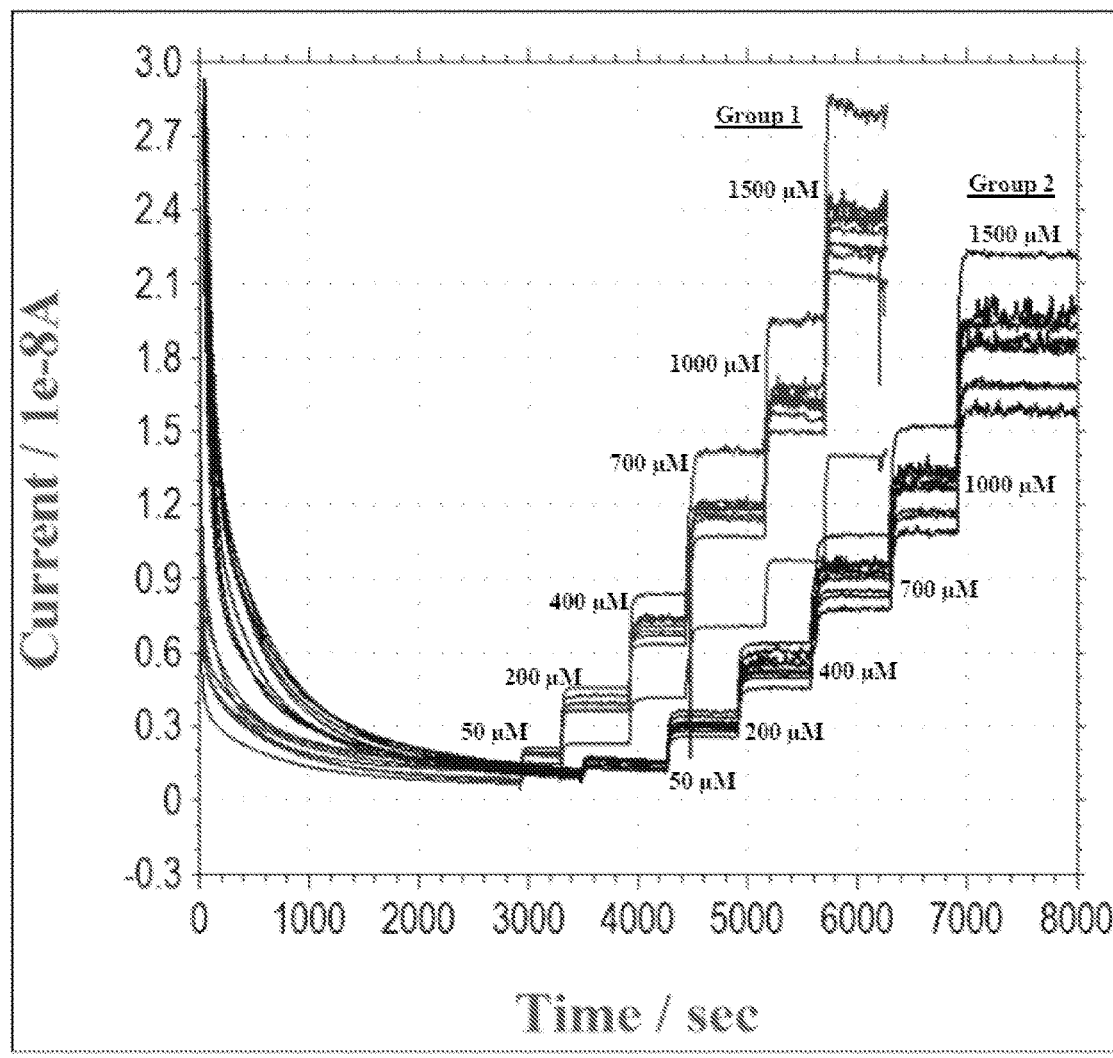

ANALYTE SENSORS WITH ETHYLENE OXIDE IMMUNITY

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. The use of an electrochemical-based analyte sensor that employs an enzyme in conjunction with integrated electronic components can allow for the quantification of an analyte in a liquid sample. Medical devices are sterilized to prevent patients from exposure to infectious disease and other harmful organisms during use of the device. Typical sterilization techniques cannot be used with some analyte sensors because they will damage either the electrical components or the enzyme.

SUMMARY

In one aspect, analyte sensors capable of undergoing sterilization with ethylene oxide are disclosed. The analyte sensors can include one or more polymer membranes having a nucleophilic group. The nucleophilic group can be a group that is nucleophilic enough to chemically react with ethylene oxide. This can be a heteroatom such as oxygen, sulfur, or nitrogen, which can be part of a functional group such as an alcohol, thiol, or amine. In some aspects, the nucleophilic group is a nitrogen atom in a polymeric subunit derived from vinyl pyridine. In other aspects, the nucleophilic group is an oxygen atom in a polymeric subunit derived from (meth) acrylate, such as 2-hydroxyethylacrylate or 2-hydroxyethylmethacrylate. In some aspects, the nucleophilic group is a negatively charged group in a polymeric subunit, such as a carboxylate or sulfonate salt. Also provided are methods for the ethylene oxide sterilization of the analyte sensors described herein.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 is a graph comparing currents produced by glucose sensors that were sterilized with ethylene oxide (EtO) at 37° C. for 6 hours at 750 mg/L concentration (Group 1) with glucose sensors that were not sterilized (Group 2).

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In one aspect, an analyte sensor capable of retaining function following sterilization with ethylene oxide (EtO) is provided. The analyte sensor can include:

a polymer membrane having a nucleophilic group; and
an analyte sensing component embedded in the polymer membrane,
wherein the nucleophilic group is able to chemically react with ethylene oxide.

In some embodiments, the analyte sensor includes two or more polymer membranes having a nucleophilic group.

Also provided are methods of sterilizing an analyte sensor with ethylene oxide. In one aspect, a method for sterilizing an analyte sensor includes:

contacting an analyte sensor with ethylene oxide,
wherein the analyte sensor includes:
a polymer membrane having a nucleophilic group; and
an analyte sensing component embedded in the polymer membrane.

In some embodiments, the nucleophilic group is nucleophilic enough to chemically react with ethylene oxide. Suitable nucleophiles include functional groups having one or more heteroatoms. Suitable heteroatoms include oxygen, nitrogen or sulfur atoms, which can be part of a functional group such as an alcohol, amine or thiol, respectively.

In another aspect, an analyte sensor is disclosed. The analyte sensor can include:

a polymer membrane having one or more nucleophilic groups; and
an analyte sensing component embedded in the polymer membrane,
wherein
at least a portion of the nucleophilic groups have reacted with ethylene oxide.

Medical devices are often sterilized to reduce the possibility of exposure to infectious, and/or harmful organisms during use. There are a number of standard sterilization methods available to sterilize medical devices, including, for example, E-beam radiation, ethylene oxide (EtO), and high temperature autoclave. But for a device having an analyte sensing component and integrated electronic components, most sterilization techniques cannot be used. For example, E-beam sterilization can damage the IC chip components, and autoclave can damage the analyte sensing component and the electronics. EtO sterilization does not damage the electronic components, but is not compatible with certain analyte sensing components (e.g., enzymes). However, as disclosed herein, if the analyte sensing component can be embedded in a polymeric material having a plurality of nucleophilic groups capable of being alkylated by ethylene oxide. These nucleophilic groups can then serve as interceptors for the ethylene oxide molecules entering the device during the sterilization process, thus protecting the analyte sensing component from being alkylated by ethylene oxide and retaining its function in the device.

In some embodiments, the analyte sensor is an enzyme-based biosensor. These devices are able to convert an analyte-concentration-dependent biochemical reaction signal into a measurable physical signal, such as an optical or electrical signal. Analyte sensors can be used in the detection of analytes in clinical, environmental, agricultural and biotechnological applications. Analytes that can be measured in clinical assays of fluids of the human body include, for example, glucose, lactate, cholesterol, bilirubin, proteins, lipids and electrolytes. The detection of analytes in biological fluids, such as blood, tear film, or intestinal fluid, can be important in the diagnosis and the monitoring of many diseases.

In some embodiments, the analyte sensor can be a component of a body-mountable device, such as an eye-mountable, tooth-mountable, or skin-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may include a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may include a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The analyte sensor can have an analyte sensing component embedded, i.e., surrounded by one or more of the polymer membranes described herein. The analyte sensing component of the analyte sensor can be selected to monitor physiological levels of a specific analyte. For example, glucose, lactate, cholesterol and various proteins and lipids can be found in body fluids, including, for example, tear film, and can be indicative of medical conditions that can benefit from continuous or semi-continuous monitoring.

The analyte sensing component can be an enzyme selected to monitor one or more analytes. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a copolymer including glucose oxidase ("GOx") can be situated around the working electrode to catalyze a reaction with glucose to produce hydrogen peroxide ($H_2O_2$). As shown below, the hydrogen peroxide can then be oxidized at the working electrode to release electrons to the working electrode, which generates a current.

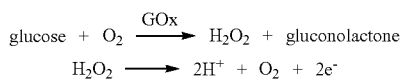

$$\text{glucose} + O_2 \xrightarrow{\text{GOx}} H_2O_2 + \text{gluconolactone}$$
$$H_2O_2 \longrightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In other embodiments, the analyte sensing component is glucose dehydrogenase (GDH). In certain instances, the use of GDH can include the addition of a cofactor such as flavin adenine dinucleotide (FAD), nicotinamide adenine dinucleotide (NAD), flavin mononucleotide, pyrroloquinoline quinone (PQQ) or a coenzyme.

The analyte sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

Ethylene oxide (EtO) is a highly strained, chemically reactive cyclic ether molecule consisting of two carbon ethylene unit and an oxygen atom. The highly stained tri-atom ring can react with nucleophilic reagents to undergo a ring opening reaction. Its sterilization effect is realized through the alkylation of nucleophilic groups on the proteins and nucleic acids of microorganisms. As a result, ethylene oxide can kill viruses, bacteria, fungi and bacterial spores.

The EtO sterilization can be performed a number of ways, and can be performed in a closed container or chamber (i.e., a "sterilizer"). Some methods as known in the art include, for example, gas diffusion sterilization, micro-dose sterilization or flexible chamber sterilization. In some methods, the ethylene oxide is introduced as a gas, while in other methods, the ethylene oxide is introduced as a liquid or a solution. The sterilization can be performed on a small scale, (i.e., a single sensor at a time), large scale (i.e., a palette- or truck-load of sensors at a time), or any scale in between.

The sterilization can be performed between about 20° C. and about 70° C. In some embodiments, the temperature can be between about 30° C. and about 60° C., or about 40° C. to about 50° C. In certain embodiments, the sterilization temperature is about 37° C.

The concentration of ethylene oxide in the sterilizer can be between about 200 mg/L and about 1,000 mg/L. In some embodiments, the concentration can be between about 200 mg/L and about 500 mg/L, or about 500 mg/L and about 1,000 mg/L. In certain embodiments, the ethylene oxide concentration is about 750 mg/L.

Because ethylene oxide can chemically react with water, the concentration of ethylene oxide in the sterilizer may be adjusted according with the humidity in the sterilizer. In some embodiments, the sterilization is performed in an atmosphere with a humidity of about 20% to about 80% humidity. When sterilization is performed in an atmosphere with a humidity above about 80% or below about 20%, the concentration of the ethylene oxide used in the sterilization may need to be adjusted to account for the reactivity of ethylene oxide with water. For example, when sterilization is carried out in humidity higher than about 80% humidity, a greater concentration of ethylene oxide may be used, and when sterilization is carried out in humidity less than about 20% humidity, a lower concentration of ethylene oxide may be used.

In some embodiments, the nucleophilic group can be a nitrogen atom in a polymeric subunit derived from vinyl pyridine, such as poly(vinyl pyridine). The nucleophilic group can be present in a crosslinked, hydrophilic copolymer of poly(ethylene glycol) (PEG) and poly(vinyl pyridine) (PVP). The copolymer of PEG and PVP can be a block copolymer, having one or more blocks each of PEG and PVP, such as a diblock copolymer of PEG and PVP.

In some embodiments, the polymer membrane having a nucleophilic group can be a crosslinked, hydrophilic, diblock copolymer of formula (I):

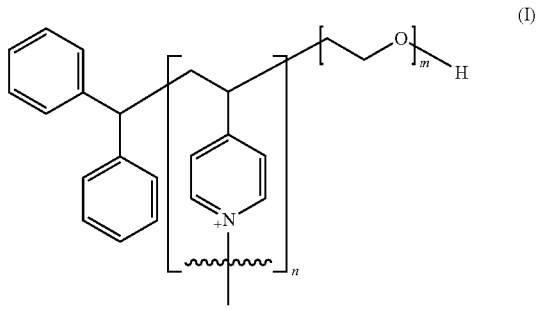

(I)

wherein n and m are independently selected to provide poly(vinyl pyridine) and poly(ethylene glycol) blocks each having number average molecular weights ($M_n$) of about 500 to about 10,000. In other embodiments, n is an average value of from about 5 to about 100, and m is an average value of from about 5 to about 250. For ease of illustration, the pyridine nitrogen of the poly(vinyl pyridine) of the sensing membrane is drawn as being covalently bound to a crosslink (i.e., crosslinked) that is described herein. One of skill in the art will recognize that, in practice, not every pyridine nitrogen may be crosslinked, and it is the uncrosslinked pyridine nitrogen atoms that can act as the nucleophile in the chemical reaction with ethylene oxide. In a similar manner, the terminal hydroxyl group of the PEG block can be the nucleophile. The cross-links are not included in the molecular weight determination.

In certain embodiments, n is selected so that the $M_n$ of the poly(vinyl pyridine) blocks falls within a range in Table 1, and m is selected so that the $M_n$ of the poly(ethylene glycol) blocks falls within a range in the Table 2. For example, the crosslinked, hydrophilic, diblock copolymer of the sensing membrane can have a poly(vinyl pyridine) block with an $M_n$ between about 5,000 and about 6,000, and a poly(ethylene glycol) block with an $M_n$ between about 8,000 and about 9,000.

TABLE 1

$M_n$ range of poly(vinyl pyridine) block (values are approximate).

| Low | High |
|---|---|
| 500 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

TABLE 2

$M_n$ range of poly(ethylene glycol) block (values are approximate).

| Low | High |
|---|---|
| 500 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the ratio of the average number of vinyl pyridine units (corresponding to n) to the average number of ethylene glycol units (corresponding to m) can be selected from Table 3. For example, when the average number of vinyl pyridine units is approximately 2,000, and the average number of ethylene glycol units can be approximately 4,000, the resulting ratio of vinyl pyridine units to ethylene glycol units is approximately 1:2.

TABLE 3

Ratio of vinyl pyridine units to ethylene glycol units (all values are approximate).

| vinyl pyridine | ethylene glycol |
|---|---|
| 1 | 1 |
| 1 | 2 |
| 1 | 3 |
| 1 | 4 |
| 1 | 5 |
| 2 | 3 |
| 3 | 4 |
| 1 | 10 |
| 1 | 20 |
| 1 | 50 |
| 1 | 100 |

In some embodiments, the polymer membrane having a nucleophilic group can be a crosslinked, hydrophilic, diblock copolymer of formula (Ia):

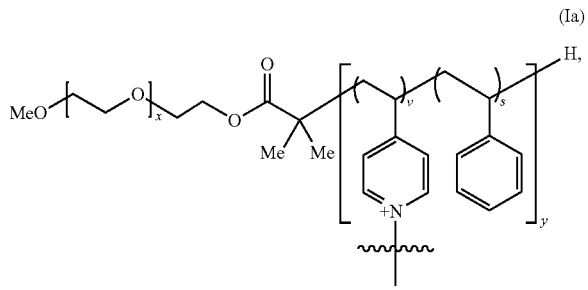

(Ia)

wherein x, y, v and s are selected such that the poly(ethylene glycol) block and the vinyl pyridine/styrene copolymer block each have a number average molecular weight ($M_n$) of about 1,000 to about 100,000. In other embodiments, x is an average value of from about 25 to about 250, and y is an average value of from about 5 to about 50. As with formula (I), the pyridine nitrogen of the poly(vinyl pyridine) of the protective membrane is drawn as being covalently bound to a crosslink for ease of illustration. But one of skill in the art will recognize that, in practice, not every pyridine nitrogen of the protective membrane will be crosslinked, and it is the uncrosslinked pyridine nitrogen atoms that can act as the nucleophile in the chemical reaction with ethylene oxide.

In some embodiments, the nucleophilic group can be included in a polymeric subunit derived from (meth)acrylate. As used herein, "(meth)acrylate" refers to acrylate, methacrylate, or mixtures thereof. The (meth)acrylate-derived unit can be part of a (meth)acrylate-derived backbone of a crosslinked, hydrophilic copolymer, where each (meth)acrylate-derived unit has a hydrophilic side chain. The hydrophilic side chains can be water soluble or soluble in a water-miscible solvent, such as an alcohol, and can have one or more heteroatoms, for example, nitrogen, oxygen or sulfur atoms. In some embodiments, the hydrophilic side chains have one or more hydroxy groups. The hydrophilic side chains of the (meth)acrylate-derived units can also include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the hydrophilic side chains is a block copolymer including blocks of two or three different poly(alkylene oxide) polymers. In certain embodiments, the poly(alkylene oxide) is block copolymer of poly(ethylene glycol) and poly(propylene glycol). In other embodiments, the hydrophilic side chains and the crosslinks both include poly(ethylene glycol).

In some embodiments, the (meth)acrylate-derived units can have the structure of formula (II):

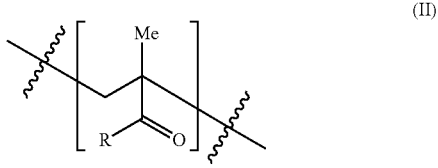

(II)

where R is a hydrophilic group having one or more nucleophilic groups. In certain embodiments, the hydrophilic group includes one or more hydroxy groups, such as an alcohol.

In some embodiments, the (meth)acrylate-derived units can have the structure of formula (IIa):

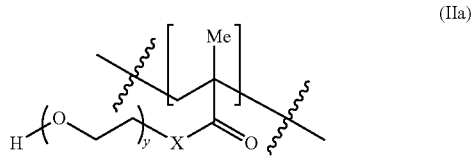

(IIa)

where X is —O—, —NR'— or —S—, and y is 0, 1, 2, 3, 4, 5, 6, 7, 8, 9 or 10, where R' is hydrogen or —C$_1$-C$_{12}$alkyl.

In some embodiments, the (meth)acrylate-derived units can be derived from 2-hydroxyethylacrylate or 2-hydroxyethylmethacrylate. In certain embodiments, the (meth)acrylate-derived units have the structure:

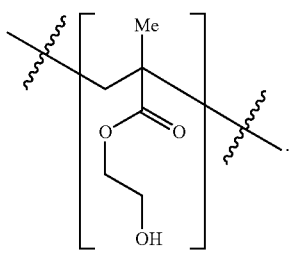

In some embodiments, the (meth)acrylate-derived units can have the structure of formula (IIa) where z is an average value of from about 2 to about 250.

In some embodiments, the (meth)acrylate-derived units can have the structure of formula (IIa) where Y and R$^2$ are as described above and x is such that the poly(ethylene glycol) has a number average molecular weight (M$_n$) of about 100 to about 10,000. In certain embodiments, x is selected so that the M$_n$ of the poly(ethylene glycol) falls within a range in Table 4.

TABLE 4

M$_n$ range of poly(ethylene glycol) in the (meth)acrylate-derived units (values are approximate).

| Low | High |
| --- | --- |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the analyte sensor has (meth)acrylate-derived units having the structure of formula (IIa), where Y is —O—, R$^2$ is methyl and x is such that the poly(ethylene glycol) has a number average molecular weight (M$_n$) of about 500.

In some embodiments, the nucleophilic group can be negatively charged. The negatively charged group can be a heteroatom, or group containing a heteroatom, that has a negative charge. The negatively charged group can also have more than one negative charge, such as a malonate. The negatively charged group can be a salt, and include one or more cations, which can include Group I and II metals as well as organic cations such as quaternary amines.

In some embodiments, a negatively charged nucleophilic group can be included in the (meth)acrylate-derived units of one or more of the polymeric membranes, and can have the structure of formula (III):

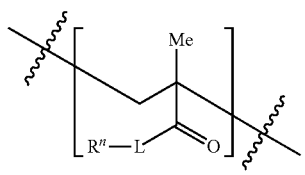

(III)

where L is a bond, $C_1$-$C_6$alkyl, —Y—$C_1$-$C_6$alkyl or a hydrophilic group, and R″ is a negatively charged group, where Y is Y is —O—, —NR'— or —S—, and R' is hydrogen or —$C_1$-$C_{12}$alkyl.

The hydrophilic group can be soluble in water or a water-miscible solvent, such as an alcohol. It can have one or more heteroatoms, for example, nitrogen, oxygen or sulfur atoms. In some embodiments, L has one or more hydroxy groups.

In some embodiments, L is $C_1$-$C_6$alkyl or —O—$C_1$-$C_6$alkyl, where $C_1$-$C_6$alkyl is methylene, ethylene, propylene, butylene, pentylene or hexylene.

In some embodiments, the negatively charged group can be included in (meth)acrylate-derived units having the structure of formula (IIIa):

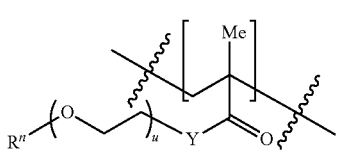

(IIIa)

where Y and R″ are as described herein and u is 1, 2, 3, 4, 5, 6, 7, 8, 9 or 10.

In some embodiments, the methacrylate-derived units can have the structure of formula (IIIa) where Y and R″ are as described above and u is such that the poly(ethylene glycol) has a number average molecular weight ($M_n$) of about 100 to about 10,000. In certain embodiments, u is selected so that the $M_n$ of the poly(ethylene glycol) falls within a range in Table 5.

TABLE 5

$M_n$ range of poly(ethylene glycol) in the fourth methacrylate-derived units (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the analyte sensor has methacrylate-derived units having the structure of formula (IIIa), where Y is —O—, R″ is methyl and u is such that the poly(ethylene glycol) has a number average molecular weight ($M_n$) of about 500.

In some embodiments, R″ is a heteroatom, or group containing a heteroatom, that has a negative charge. R″ can be a group having more than one negative charge, such as a malonate. R″ can be a salt, and include one or more cations, which can include Group I and II metals as well as organic cations such as quaternary amines. R″ can be chosen from —O⁻, —S⁻, —N(R')⁻, —C(O)O⁻, —N(R')C(O)O⁻, —S(O)(R')⁻, —S(O)O⁻, —S(O)$_2$O⁻, —P(O)(OR')O⁻, —P(O)(R')O⁻, —P(O)(NR$_2$)O⁻, —P(O)(NR$_2$')(NR')⁻, —P(O)(R')(NR')⁻, —P(O)(OR')(NR')⁻, —OP(O)(OR') O⁻, —OP(O)(R') O⁻, —OP(O)(NR$_2$') O⁻, —OP(O)(NR$_2$')(NR')⁻, —OP(O)(R')(NR')⁻, —OP(O)(OR')(NR')⁻, —P(O)O$_2^{2-}$, —P(O)(NR')$_2^{2-}$, —OP(O)O$_2^{2-}$, —OP(O)(NR')$_2^{2-}$ or a salt thereof, where R' is hydrogen or —$C_1$-$C_{12}$alkyl. In some embodiments, -L-R″ is an alkylsulfonate salt, such as potassium propylsulfonate. In other embodiments, L is a bond and R″ is O⁻ or a salt thereof.

In some embodiments, the analyte sensors can include a membrane of crosslinked proteins, and the nucleophilic group can be a functional group on one or more of the proteins. The proteins of can be substantially unreactive in biochemical reactions, which will limit interference with the analyte sensing component, but may include nucleophilic groups capable of chemical reaction with ethylene oxide. The proteins can be covalently bound through crosslinks, forming a crosslinked network. The crosslinks can have covalent bonds between the proteins, and can also include covalent bonds between the analyte sensing component and one or more proteins and/or another analyte sensing component. One or more of the polymer membranes can have one or more proteins. In some embodiments, the proteins are the same, or substantially the same, while in other embodiments, sensing membrane can have two or more different types of proteins. In some embodiments, the proteins are bovine serum albumin.

In some embodiments, the nucleophilic group can be a functional group on one or more crosslinks in one or more of the polymer membranes. The crosslinks can be present between the pyridine nitrogen atoms of formulae (I) and (Ia) or between the nitrogen atoms of the amine groups in a membrane having crosslinked proteins.

The crosslinks can be derived from crosslinking agents containing two or more epoxide groups. Chemical reaction of the epoxides with the crosslinkable functionalities of the copolymer of the sensing membrane and/or the copolymer of the protective membrane can proceed through nucleophilic attack of the crosslinkable functionality at the electrophilic epoxide carbon atom, providing a crosslink containing two or more secondary alcohol moieties. For example, a copolymer having nitrogen functionalities, such as a pyridine group, can react with a crosslinking agent having epoxide groups to provide crosslinks containing β-hydroxy amine functionalities.

In some embodiments, the crosslinks include poly(ethylene glycol) (PEG). For example, the crosslinks can have the structure of formula (IV):

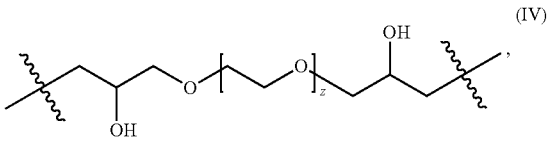

(IV)

wherein z is 0, 1, 2, 3, 4, 5, 6, 7, 8, 9 or 10.

In certain embodiments, z is an average value of from about 5 to about 250.

In other embodiments, z is such that the number average molecular weight ($M_n$) of the PEG portion of the crosslinks is about 200 to about 10,000. For example, z can be selected such that the $M_n$ of the PEG portion of the crosslinks falls within a range in Table 6:

TABLE 6

$M_n$ range of the poly(styrene) (PEG) of the crosslinks (values are approximate).

| Low | High |
| --- | --- |
| 100 | 500 |
| 500 | 1,000 |
| 1,000 | 2,000 |
| 2,000 | 3,000 |
| 3,000 | 4,000 |
| 4,000 | 5,000 |
| 5,000 | 6,000 |
| 6,000 | 7,000 |
| 7,000 | 8,000 |
| 8,000 | 9,000 |
| 9,000 | 10,000 |

Suitable crosslinks are derived from, for example, diglycidyl ether, N,N-diglycidyl-4-glycidyloxyaniline, and diethylene glycol diglycidyl ether.

In some embodiments, the crosslinks can be formed through carbon-nitrogen double bonds between the nitrogen atoms of amine groups on the proteins and/or analyte sensing component and carbon atoms in the crosslinks. In some embodiments, the crosslinks can be derived from di-carbonyl compounds. For example, the crosslinks of the sensing membrane can have the structure of formula (V):

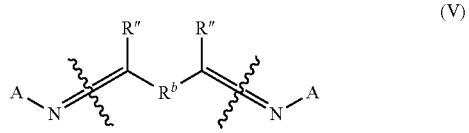

(V)

where A is independently a protein or an analyte sensing component, $R^b$ is $C_0$-$C_4$alkyl or a hydrophilic group and R" is independently hydrogen or —$C_1$-$C_{12}$alkyl, where $R^b$ includes one or more nucleophilic groups. $R^b$ can be soluble in water or a water-miscible solvent, such as an alcohol, and can have one or more heteroatoms (e.g., nitrogen, oxygen or sulfur). In some embodiments, the crosslinks have one or more hydroxy groups. For example, $R^b$ can have the structure of formula (IV). It is understood from formula (V) that the crosslinks have two carbons in addition to the $R^b$ group. Thus, crosslinks referred to herein as having a certain number of carbon atoms (e.g., $C_4$) will have an $R^b$ group with two less carbon atoms (e.g., $C_2$). For example, "$C_4$alkyl crosslinks" have an $R^b$ group that is $C_2$alkyl.

In some embodiments, the crosslinks include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks and the (meth)acrylate-derived units include poly(ethylene glycol).

EXAMPLES

Example 1. Preparation and Sterilization of an Analyte Sensor

A solution of glucose oxidase (10 mg, type VII, Sigma) in PBS (400 uL) was mixed with HEMA (225 uL), PEGMA (175 uL), diethyleneglycol dimethacrylate (4 uL), and 2,2-dimethoxy-2-phenylacetophenone (2 mg). The resulting mixture was deposited onto platinum electrodes and cured with 365 nm UV light for 5 minutes to provide a glucose sensor. A number of sensors were made in the same way. A group of the sensors (Group 1) underwent EtO sterilization (at 37° C. for 6 hours at 750 mg/L). Another group (Group 2) were stored under ambient conditions without sterilization. Groups 1 and 2 were tested at concentrations of glucose in phosphate buffered saline (PBS) ranging from 50 μM to 1500 μm. The sensors were submerged in PBS and the glucose concentration was increased every 10-15 minutes. The current generated at the electrode of each sensor was measured using a potentiostat (FIG. 1).

The invention claimed is:

1. An analyte sensor comprising:
   a polymer membrane comprising (meth)acrylate-derived units having a negatively charged nucleophilic group; and
   an analyte sensing component embedded in the polymer membrane,
   wherein the analyte sensor has been sterilized with ethylene oxide, and
   wherein the negatively charged nucleophilic group is —$S^-$, —$N(R')C(O)O^-$, —$S(O)(R')^-$, —$S(O)O^-$, —$P(O)(OR')O^-$, —$P(O)(R')O^-$, —$P(O)(NR'_2)O^-$, —$P(O)(NR'_2)(NR')^-$, —$P(O)(R')(NR')^-$, —$P(O)(OR')(NR')^-$, —$OP(O)(OR')O^-$, —$OP(O)(R')O^-$, $OP(O)(NR'_2)O^-$, —$OP(O)(NR'_2)(NR')^-$, —$OP(O)(R')(NR')^-$, —$OP(O)(OR')(NR')^-$, —$P(O)O_2^{2-}$, —$P(O)(NR')_2^{2-}$, —$OP(O)O_2^{2-}$, —$OP(O)(NR')_2^{2-}$ or a salt thereof, wherein R' is hydrogen or —$C_1$-$C_{12}$alkyl.

2. The analyte sensor of claim 1, wherein the analyte sensor has been sterilized with ethylene oxide in an atmosphere of about 20% to about 80% humidity.

3. The analyte sensor of claim 1, wherein the analyte sensor has been sterilized with ethylene oxide in an atmosphere of below 20% humidity and at an ethylene oxide concentration between about 200 mg/L and about 500 mg/L.

4. The analyte sensor of claim 1, wherein the analyte sensor has been sterilized with ethylene oxide in an atmosphere of above 80% humidity and at an ethylene oxide concentration between about 500 mg/L and about 1,000 mg/L.

5. The analyte sensor of claim 1, wherein the analyte sensor has been sterilized with ethylene oxide at a temperature between about 20° C. and about 70° C.

6. The analyte sensor of claim 1, wherein the negatively charged nucleophilic group is a component of a salt.

7. The analyte sensor of claim 1, wherein the (meth)acrylate-derived unit has the structure of formula (III):

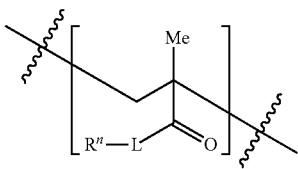

(III)

wherein
L is a bond, $C_1$-$C_6$alkyl, —Y—$C_1$-$C_6$alkyl or a hydrophilic group, wherein Y is —O—, —NR'— or —S—, and R' is hydrogen or —$C_1$-$C_{12}$alkyl; and
R" is the negatively charged nucleophilic group.

8. A method for sterilizing an analyte sensor, comprising: contacting the analyte sensor with ethylene oxide, wherein the analyte sensor comprises:
   a polymer membrane comprising (meth)acrylate-derived units having a negatively charged nucleophilic group; and
   an analyte sensing component embedded in the polymer membrane,
   wherein the negatively charged nucleophilic group is —S⁻, —N(R')C(O)O⁻, —S(O)(R')⁻, —S(O)O⁻, —P(O)(OR')O⁻, —P(O)(R')O⁻, —P(O)(NR'$_2$)O⁻, —P(O)(NR'$_2$)(NR')⁻, —P(O)(R')(NR')⁻, —P(O)(OR')(NR')⁻, —OP(O)(OR')O⁻, —OP(O)(R')O⁻, —OP(O)(NR'$_2$)O⁻, —OP(O)(NR'$_2$)(NR')⁻, —OP(O)(R')(NR')⁻, —OP(O)(OR')(NR')⁻, —P(O)O$_2$²⁻, —P(O)(NR')$_2$²⁻, —OP(O)O$_2$²⁻, —OP(O)(NR')$_2$²⁻ or a salt thereof, wherein R' is hydrogen or —$C_1$-$C_{12}$alkyl.

9. The method of claim 8, wherein the contacting occurs in an atmosphere of about 20% to about 80% humidity.

10. The method of claim 8, wherein the contacting occurs in an atmosphere of below 20% humidity and at an ethylene oxide concentration between about 200 mg/L and about 500 mg/L.

11. The method of claim 8, wherein the contacting occurs in an atmosphere of above 80% humidity and at an ethylene oxide concentration between about 500 mg/L and about 1,000 mg/L.

12. The method of claim 8, wherein the contacting occurs at a temperature between about 20° C. and about 70° C.

13. The analyte sensor of claim 7, wherein L is $C_1$-$C_6$alkyl or —O—$C_1$-$C_6$alkyl.

14. The method of claim 8, wherein the (meth)acrylate-derived unit has the structure of formula (III):

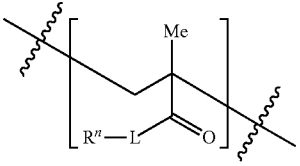

(III)

wherein
L is a bond, $C_1$-$C_6$alkyl, —Y—$C_1$-$C_6$alkyl or a hydrophilic group, wherein Y is —O—, —NR'— or —S—, and R' is hydrogen or —$C_1$-$C_{12}$alkyl; and
R" is the negatively charged nucleophilic group.

15. The method of claim 14, wherein L is $C_1$-$C_6$alkyl or —O—$C_1$-$C_6$alkyl.

* * * * *